United States Patent
Basu et al.

(10) Patent No.: US 7,711,910 B1
(45) Date of Patent: *May 4, 2010

(54) FLEXIBLE QUEUE AND STREAM MAPPING SYSTEMS AND METHODS

(75) Inventors: Debashis Basu, San Jose, CA (US); Avanindra Godbole, San Jose, CA (US)

(73) Assignee: Juniper Networks, Inc., Sunnyvale, CA (US)

( * ) Notice: Subject to any disclaimer, the term of this patent is extended or adjusted under 35 U.S.C. 154(b) by 459 days.

This patent is subject to a terminal disclaimer.

(21) Appl. No.: 11/676,705

(22) Filed: Feb. 20, 2007

Related U.S. Application Data (63) Continuation of application No. 10/206,993, filed on Jul. 30, 2002, now Pat. No. 7,197,612.

(60) Provisional application No. 60/348,619, filed on Jan. 17, 2002.

(51) Int. Cl.
 G06F 12/00 (2006.01)
 G06F 15/16 (2006.01)
 H04L 12/00 (2006.01)

(52) U.S. Cl. ............... 711/156; 370/351; 709/231

(58) Field of Classification Search ............... None
See application file for complete search history.

(56) References Cited

U.S. PATENT DOCUMENTS

| | | | | |
|---|---|---|---|---|
| 6,092,115 | A | 7/2000 | Choudhury et al. | 709/235 |
| 6,452,933 | B1 | 9/2002 | Duffield et al. | 370/415 |
| 6,473,424 | B1 | 10/2002 | DeJager et al. | 370/389 |
| 6,643,298 | B1 | 11/2003 | Brunheroto et al. | 370/537 |
| 6,680,933 | B1 | 1/2004 | Cheesman et al. | 370/352 |
| 6,975,638 | B1 | 12/2005 | Chen et al. | 370/412 |
| 7,050,448 | B2 | 5/2006 | Johnson et al. | 370/413 |
| 7,197,612 | B1 * | 3/2007 | Basu et al. | 711/156 |

* cited by examiner

*Primary Examiner*—Denise Tran
(74) *Attorney, Agent, or Firm*—Harrity & Harrity, LLP (57) ABSTRACT

A system processes data corresponding to multiple data streams. The system includes multiple queues that store the data, stream-to-queue logic, dequeue logic, and queue-to-stream logic. Each of the queues is assigned to one of the streams based on a predefined queue-to-stream assignment. The stream-to-queue logic identifies which of the queues has data to be processed. The dequeue logic processes data in the identified queues. The queue-to-stream logic identifies which of the streams correspond to the identified queues.

11 Claims, 8 Drawing Sheets

FLEXIBLE QUEUE AND STREAM MAPPING SYSTEMS AND METHODS

RELATED APPLICATIONS

This application is a continuation of U.S. patent application Ser. No. 10/206,993 filed Jul. 30, 2002, now U.S. Pat. No. 7,197,612, which claims priority under 35 U.S.C. §119 based on U.S. Provisional Application Ser. No. 60/348,619, filed Jan. 17, 2002, the disclosures of which are incorporated herein by reference.

BACKGROUND OF THE INVENTION

1. Field of the Invention

The present invention relates generally to data transfer and, more particularly, to systems and methods for performing flexible queue and stream mapping.

2. Description of Related Art

Conventional network devices, such as routers, transfer streams of data through a network from a source to a destination. Typically, the network devices include one or more memory subsystems to temporarily buffer data while the network devices perform network-related functions, such as route processing or accounting.

A data stream may be considered a pipe of data packets belonging to a communication between a particular source and a particular destination. A network device may assign a variable number of queues (e.g., where a queue may be considered a logical first-in, first-out (FIFO) buffer) to a data stream. For a stream with n queues, the relationship of queues and streams may be represented by:

$$\text{stream}_{bandwidth} = \sum_{0}^{n-1} \text{queue}_{bandwidth}.$$

A problem arises in conventional network devices because a large number of queues need to be flexibly assigned to a large number of streams. When a stream number is supplied, it is necessary to identify all of the queues associated with it. Similarly, when a queue number is supplied, it is necessary to identify the stream to which it is associated. As the number of streams and queues increases, it becomes difficult to quickly determine correspondence between streams and queues.

Therefore, there exists a need for systems and methods that provide queue-to-stream and stream-to-queue mapping in an efficient, cost-effective manner.

SUMMARY OF THE INVENTION

Systems and methods consistent with the principles of the invention address this and other needs by defining a maximum number of queues for each stream based on the stream number. Each queue may then be numbered and the set of streams to which the queue may possibly belong may be defined. Mapping between stream numbers and queue numbers may then be performed in an efficient and cost-effective manner.

In accordance with the principles of the invention as embodied and broadly described herein, a system processes data corresponding to multiple data streams. The system includes multiple queues that store the data, stream-to-queue logic, dequeue logic, and queue-to-stream logic. Each of the queues is assigned to one of the streams based on a predefined queue-to-stream assignment. The stream-to-queue logic identifies which of the queues has data to be processed when a stream is picked for dequeue. This helps in converting stream flow control to queue flow control. The dequeue logic processes data in the identified queues. The queue-to-stream logic identifies which stream corresponds to the identified queue.

In another implementation consistent with the present invention, a system identifies one or more queues that store data to be processed. Each of the queues is assigned to one of multiple streams of data. The system includes a mask memory, a stream state memory, first logical operators corresponding to the streams, and a second logical operator. The mask memory stores masks corresponding to the streams, where each of the masks identifies one or more of the queues assigned to the stream. The stream state memory stores one or more stream state vectors, where each of the stream state vectors identifies whether a corresponding one of the streams can accept more data. Each of the first logical operators performs a first logical operation on the mask and the stream state vector to generate a result vector for the corresponding stream. The second logical operator performs a second logical operation on the result vectors from the first logical operators to identify one or more of the queues that have data to be processed.

In yet another implementation consistent with the present invention, a system identifies a stream corresponding to an identifier for one of multiple queues. Each of the queues is assigned to one of multiple streams of data. The system includes multiplexers, a first logical operator, and a second logical operator. Each of the multiplexers receives a level vector associated with one or more of the streams and the queue identifier and outputs a data value. The first logical operator performs a first logical operation on the data values from the multiplexers to generate an output vector. The second logical operator performs a second logical operation on the queue identifier and the output vector from the first logical operator to identify one of the streams that corresponds to the queue identifier.

BRIEF DESCRIPTION OF THE DRAWINGS

The accompanying drawings, which are incorporated in and constitute a part of this specification, illustrate embodiments of the invention and, together with the description, explain the invention. In the drawings.

DETAILED DESCRIPTION

The following detailed description of the invention refers to the accompanying drawings. The same reference numbers in different drawings may identify the same or similar elements. Also, the following detailed description does not limit the invention. Instead, the scope of the invention is defined by the appended claims and equivalents of the recited claim limitations.

Systems and methods consistent with the principles of the invention provide stream-to-queue and queue-to-stream mapping in a quick and efficient manner. To facilitate the mapping, a maximum number of queues for each stream is defined based on the stream number. The queues are then numbered and the set of streams to which the queues may possibly belong are defined.

For the description that follows, it will be assumed that there are M streams and N queues. An exemplary value for M may be 128 and for N may be 256. Other values may also be chosen, such as M=256 and N=512.

Exemplary Network Device Configuration

Figure 1:
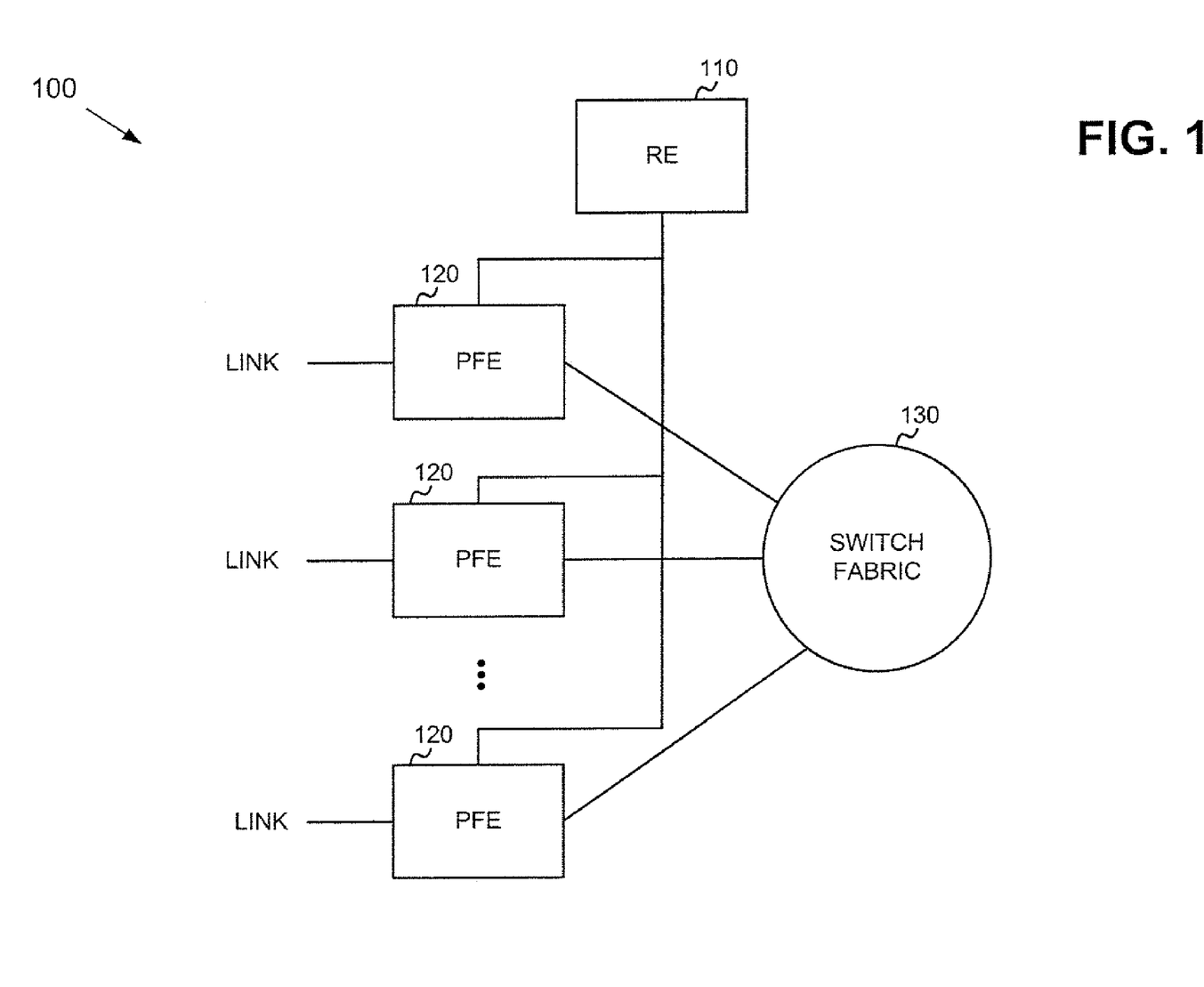
FIG. 1 is a diagram of an exemplary network device in which systems and methods consistent with the principles of the invention may be implemented.

FIG. 1 is a diagram of an exemplary network device in which systems and methods consistent with the principles of the invention may be implemented. In this particular implementation, the network device takes the form of a router 100. Router 100 may receive one or more data streams from a physical link, process the data stream(s) to determine destination information, and transmit the data stream(s) on one or more links in accordance with the destination information.

Router 100 may include a routing engine (RE) 110 and multiple packet forwarding engines (PFEs) 120 interconnected via a switch fabric 130. Switch fabric 130 may include one or more switching planes to facilitate communication between two or more of PFEs 120. In an implementation consistent with the principles of the invention, each of the switching planes includes a single or multi-stage switch of crossbar elements.

RE 110 performs high level management functions for router 100. For example, RE 110 communicates with other networks and systems connected to router 100 to exchange information regarding network topology. RE 110 creates routing tables based on network topology information, creates forwarding tables based on the routing tables, and sends the forwarding tables to PFEs 120. PFEs 120 use the forwarding tables to perform route lookup for incoming packets. RE 110 also performs other general control and monitoring functions for router 100.

Each of PFEs 120 connects to RE 110 and switch fabric 130. PFEs 120 receive data on physical links connected to a network, such as a wide area network (WAN), a local area network (LAN), or another type of network. Each physical link could be one of many types of transport media, such as optical fiber or Ethernet cable. The data on the physical link is formatted according to one of several protocols, such as the synchronous optical network (SONET) standard or Ethernet.

Figure 2:
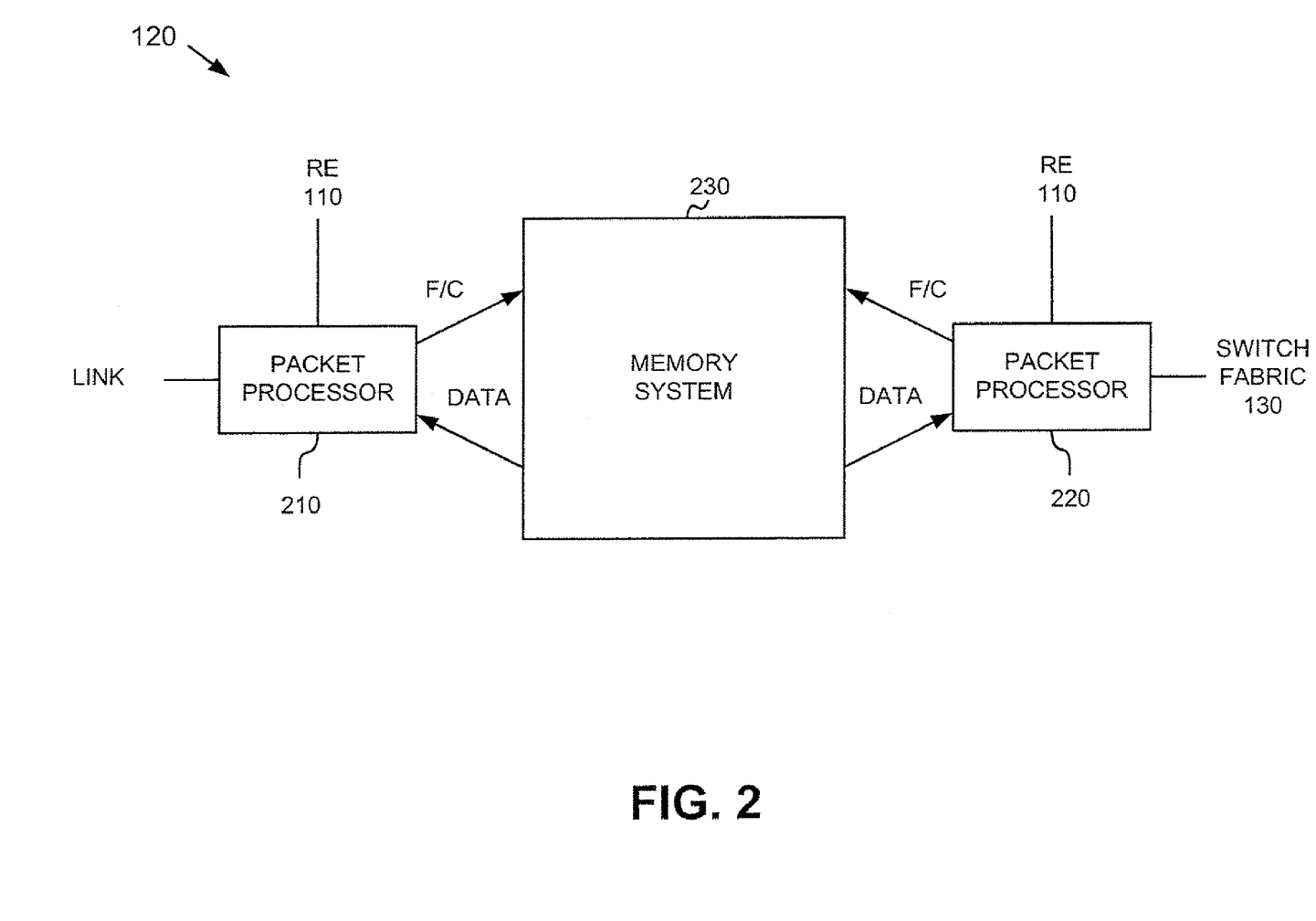
FIG. 2 is an exemplary diagram of a packet forwarding engine (PFE) of FIG. 1 according to an implementation consistent with the principles of the invention.

FIG. 2 is an exemplary diagram of a PFE 120 according to an implementation consistent with the principles of the invention. PFE 120 may include two packet processors 210 and 220, each connected to memory system 230 and RE 110. Packet processors 210 and 220 communicate with RE 110 to exchange routing-related information. For example, packet processors 210 and 220 may receive forwarding tables from RE 110, and RE 110 may receive routing information from packet processor 210 that is received from a physical link. RE 110 may also send routing-related information to packet processor 210 for transmission over the link.

Packet processor 210 connects to physical links. Packet processor 210 may process packets received from the incoming links and prepare packets for transmission on the outgoing links. For example, packet processor 210 may perform route lookup based on packet header information to determine destination information for the packets. For packets received from the link, packet processor 210 may store data in memory system 230. For packets to be transmitted on the link, packet processor 210 may read data from memory system 230.

Packet processor 220 connects to switch fabric 130. Packet processor 220 may process packets received from switch fabric 130 and prepare packets for transmission to switch fabric 130. For packets received from switch fabric 130, packet processor 220 may store data in memory system 230. For packets to be transmitted to switch fabric 130, packet processor 220 may read data from memory system 230.

Packet processors 210 and 220 may store data in queues within memory system 230. When reading data from memory system 230, packet processors 210 and 220 may transmit flow control (F/C) signals to memory system 230. The flow control signals indicate which streams are ready to receive data. A flow control signal may, for example, be a vector of size M, where M represents the number of streams. The vector may contain a number of bits, such as one bit per stream, that indicate whether the corresponding streams can receive any more data from memory system 230. In response to the flow control signal, memory system 230 may retrieve data associated with the streams and send this data to the appropriate packet processor 210 or 220.

The flow control signals and data identified in FIG. 2 are provided to facilitate description of the invention. In operation, other types of data and information may flow between packet processors 210 and 220 and memory system 230.

Figure 3:
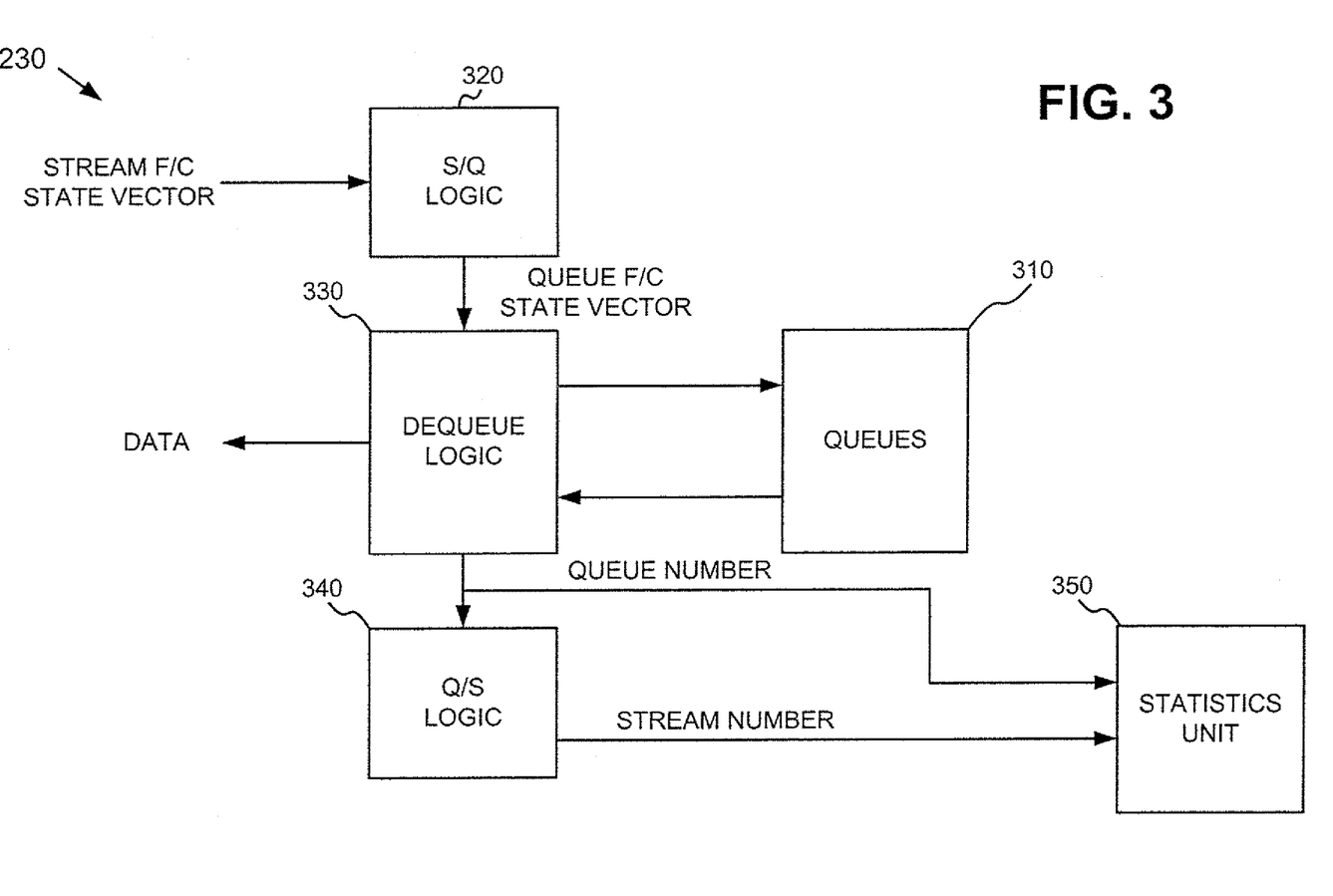
FIG. 3 is an exemplary diagram of a portion of the memory of FIG. 2 according to an implementation consistent with the principles of the invention.

FIG. 3 is an exemplary diagram of a portion of memory system 230 that acts in response to a flow control signal to retrieve data for the appropriate packet processor 210 or 220. The portion of memory system 230 includes a bank of memory queues 310, stream-to-queue (S/Q) logic 320, dequeue logic 330, queue-to-stream (Q/S) logic 340, and statistics unit 350. Queues 310 may include N queues capable of storing data for M possible streams of data.

S/Q logic 320 may include logic that converts the stream numbers identified by the flow control signals as ready to receive data to corresponding queue numbers, possibly in the form of a queue flow control state vector, for use by dequeue logic 330. Dequeue logic 330 may include logic that follows a queue service principle to identify a queue among the ones identified by the queue numbers from the S/Q logic 320, reads data from that queue, and sends the data to either packet processor 210 or 220. Dequeue logic 330 may also send the queue numbers to Q/S logic 340. Q/S logic 340 may include logic that converts the queue numbers from dequeue logic 330 to the corresponding stream numbers.

Statistics unit 350 may receive the stream numbers and queue numbers for stream level and queue level statistics monitoring, respectively. Statistics unit 350 may keep statistics on the use of queues 310 and the amount of data sent on particular streams for flow control or accounting purposes. For example, statistics unit 350 may track particular streams for assuring stream-level quality of service or monitor a queue for assuring quality of service for a particular type of traffic.

Exemplary Queue and Stream Mapping

Figure 4:
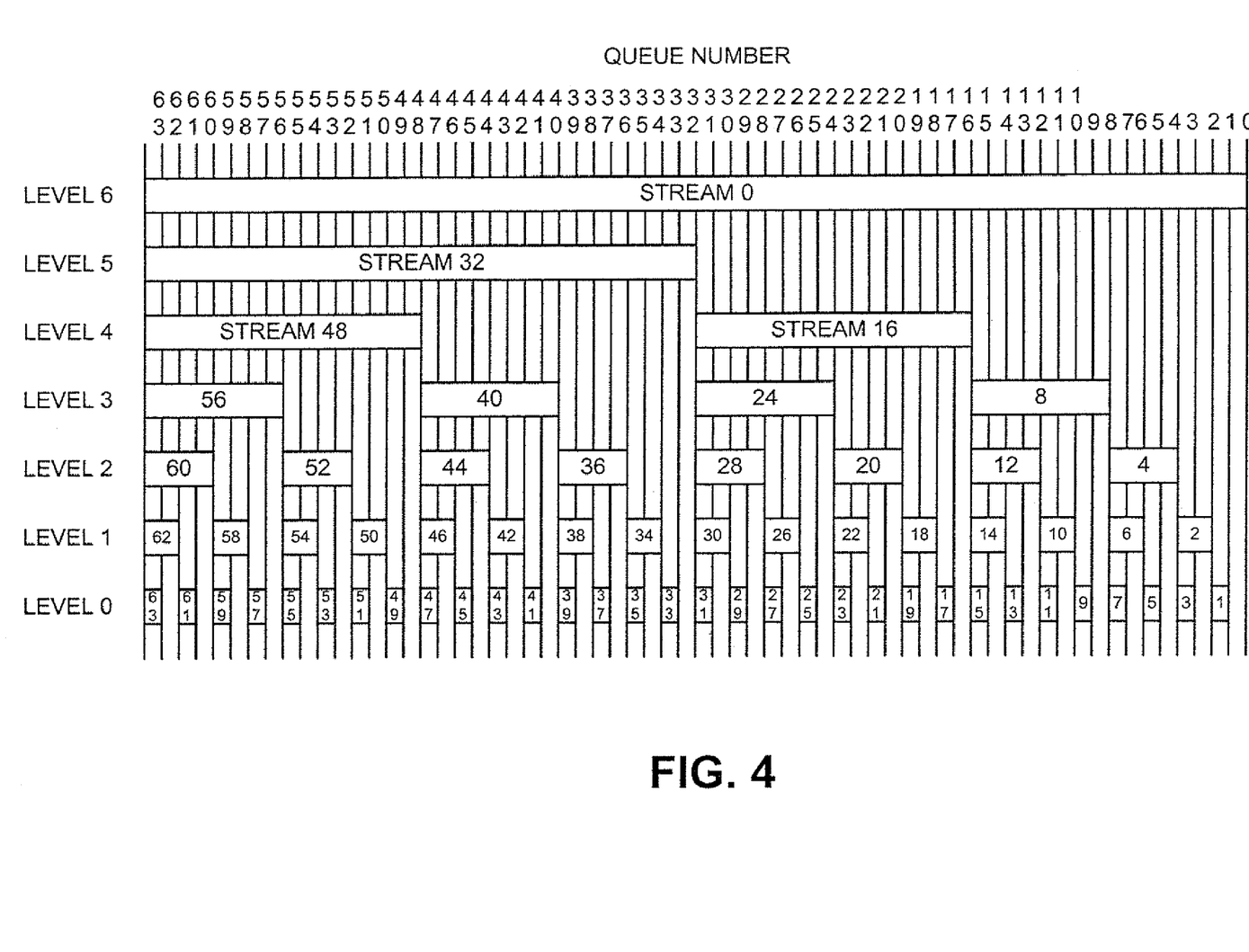
FIG. 4 is an exemplary diagram of the assignment of queues to streams according to principles consistent with the invention.

FIG. 4 is an exemplary diagram of the assignment of queues to streams consistent with the principles of the invention. To facilitate implementations consistent with the principles of the invention, a relationship between a large number of queues and a large number of streams is defined, such that each queue is assigned to a single stream. Suppose, for example, that there are 64 streams and 64 queues. A stream may consist of none, all, or any other number of the queues.

In the example shown in FIG. 4, it will be assumed that there are 64 streams. The streams may also be numbered using, for example, the first queue number that can be assigned to the stream. For example, stream 0 can have all 64 queues assigned to it; stream 32 can have queues 32-63 assigned to it; stream 16 can have queues 16-31 assigned to it; and so on. As seen from FIG. 4, the maximum number of streams that a queue can possibly belong to is 7 (e.g., queue 63 can possibly belong to streams 0, 32, 48, 56, 60, 62, or 63).

Every stream may have a bit-vector mask. The bit-vector mask for a stream may be the same size as the maximum number of queues that can be assigned to it. A bit set in this mask indicates that a specific queue is assigned to the stream. The total number of register bits needed for the bit-vector masks for the representation shown in FIG. 4 is:

$$64+32+16*2+8*4+4*8+2*16+1*32=256.$$

Figure 5:
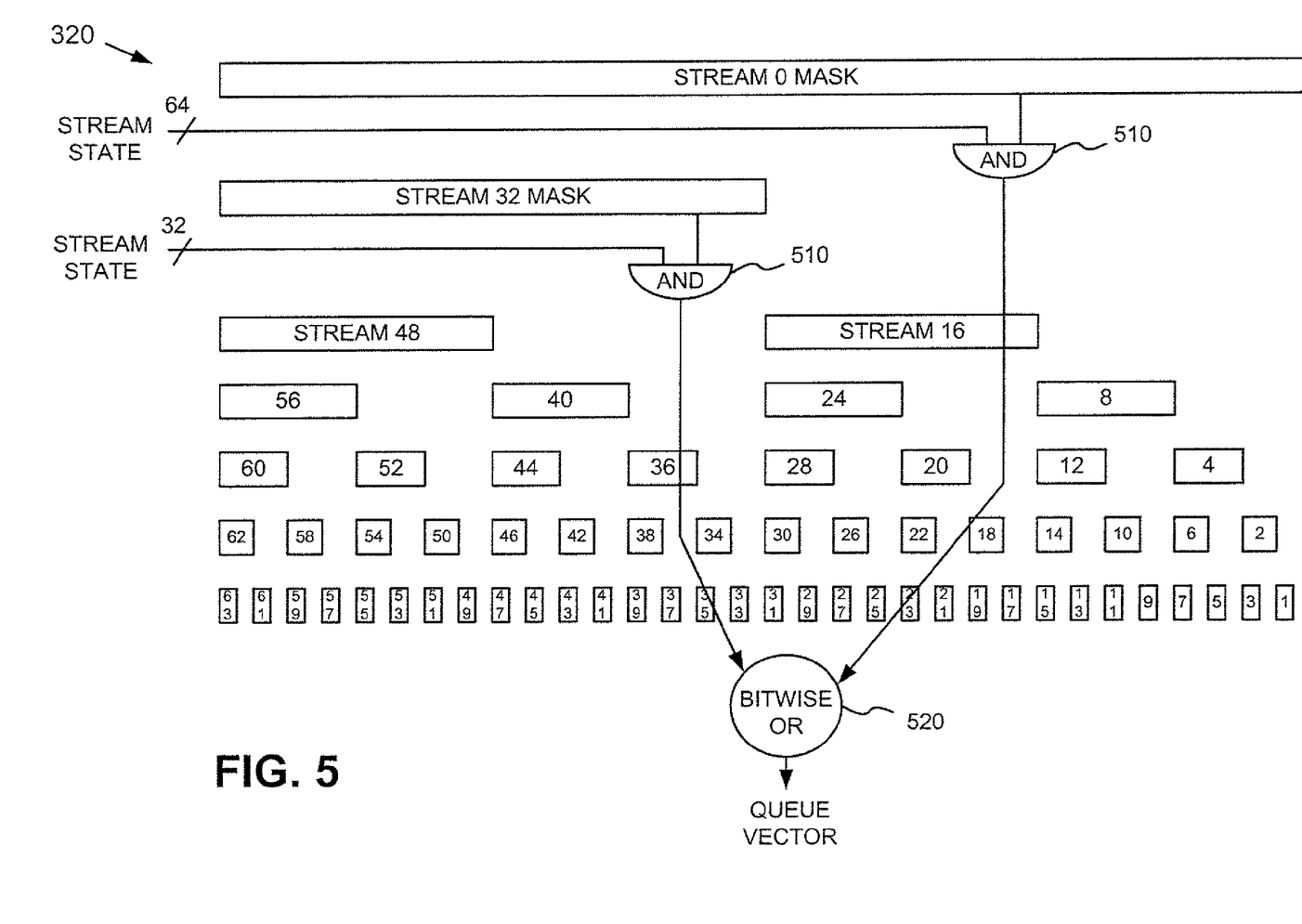
FIG. 5 is an exemplary diagram of stream-to-queue logic of FIG. 3 according to an implementation consistent with the principles of the invention.

FIG. 5 is an exemplary diagram of S/Q logic 320 according to an implementation consistent with the principles of the invention. S/Q logic 320 includes a series of AND gates 510 and an OR gate 520. Only two AND gates 510 are shown for simplicity. Each stream may include a corresponding AND gate that is coupled to OR gate 520.

Each of AND gates 510 performs an AND operation on the stream state and the mask corresponding to the stream. The stream state may be obtained from the flow control signal received by S/Q logic 320 and stored in a memory. As described above, the flow control signal is a vector that contains a number of bits, such as one bit per stream, that indicate whether the corresponding streams are ready to receive data ("stream state"). S/Q logic 320 may expand the stream state to the size of the mask for the stream.

For example, the stream state of stream 0 is expanded to a 64-bit replicated vector. AND gate 510 may then perform an AND operation on the stream state vector and the mask for stream 0 to obtain a 64-bit result vector. The stream state of stream 32 is expanded to a 32-bit replicated vector. AND gate 510 may then perform an AND operation on the stream state vector and the mask for stream 32 to obtain a 32-bit result vector. Similar operations may be performed for the other streams.

OR gate 520 may operate on the result vectors from AND gates 510. In an implementation consistent with the principles of the invention, the result vectors may be expanded to the same size, such as 64 bits. For example, the result vector for stream 32, which corresponds to queues 32-63, may be expanded to a 64 bit vector by adding predetermined bits, such as zero bits, that correspond to queues 0-31.

OR gate 520 may perform a bitwise OR function on the result vectors to generate a queue flow control state vector. The queue vector may identify which queues may contain data to be processed by dequeue logic 330. The identified queues correspond to the streams identified by the flow control signal as ready to receive more data.

Figure 6:
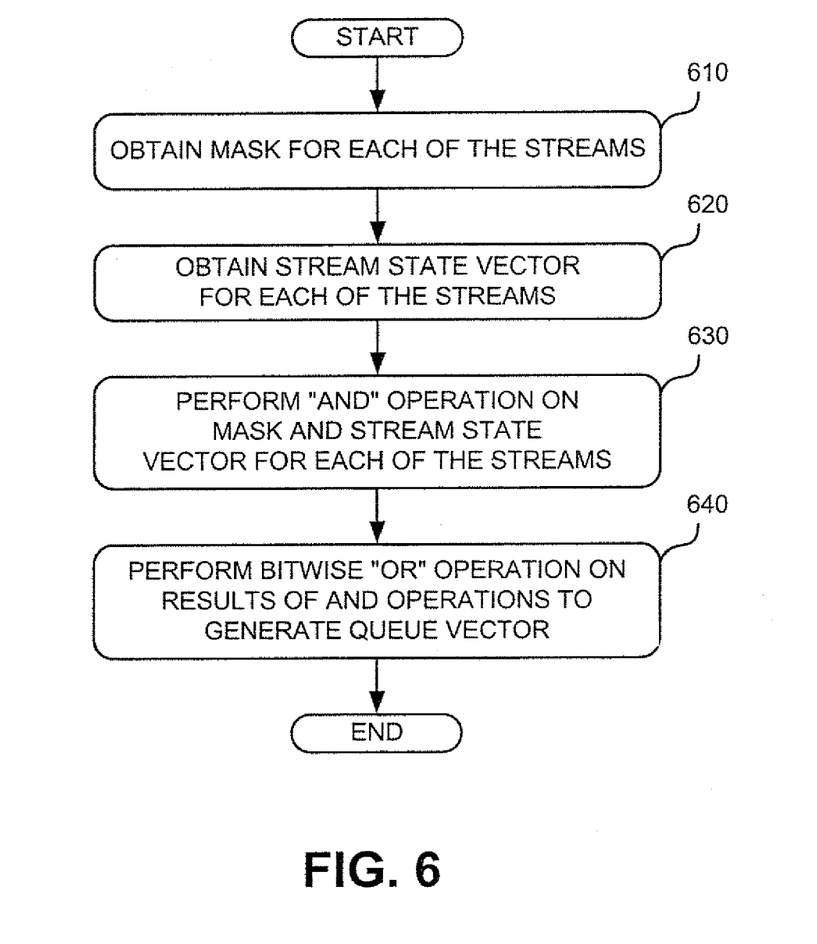
FIG. 6 is a flowchart of exemplary processing for stream-to-queue mapping according to an implementation consistent with the principles of the invention.

FIG. 6 is a flowchart of exemplary processing for stream-to-queue mapping according to an implementation consistent with the principles of the invention. Processing may begin with S/Q logic 320 obtaining the mask for each of the streams (Act 610). As described above, a mask may be associated with each of the streams based, for example, on the queue-to-stream assignment illustrated in FIG. 4. The mask associated with a stream specifies which queues are assigned to the stream.

S/Q logic 320 may obtain a stream state vector for each of the streams (Act 620). As described above, S/Q logic 320 may generate the stream state vector from the flow control signal received from a packet processor, such as packet processor 210 or 220. S/Q logic 320 may expand the bit corresponding to the stream into a replicated bit vector containing the same number of bits as the mask associated with the stream.

AND gates 510 may perform AND operations on the masks and stream state vectors for the streams (Act 630). For each stream, an AND gate 510 may AND the corresponding mask and stream state vector to generate a result vector. The result vectors may optionally be expanded to the size of the largest result vector (e.g., 64 bits).

OR gate 520 may perform a bitwise OR operation on the result vectors from AND gates 510 to generate a queue vector (Act 640). The queue vector may identify which queues may contain data to be processed by dequeue logic 330. For example, the queue vector may include a separate bit for each of the queues that indicates whether the queue may have data to be processed.

As an example, suppose that stream 16 is the only stream ready to receive data and a bit value of one indicates this ready state. Suppose further that the mask for stream 16 indicates that queues 17-20 are assigned to stream 16. In this case, the mask for stream 16 may contain the following bits: 0000000000011110. S/Q logic 320 may expand the stream state to a sixteen bit vector to match the size of the mask for stream 16. In this case, the stream state vector may contain the following bits: 1111111111111111. All other streams contain a stream state vector of all zeroes.

AND gates 510 perform bitwise AND operations on the masks and stream state vectors corresponding to the streams. The AND operations generate result vectors that contain all zeroes for each of the streams, except stream 16. The result vector for stream 16 resembles the mask for stream 16 (i.e., 0000000000011110).

OR gate 520 then performs bitwise OR operations on the result vectors from AND gates 510 to generate a queue vector, containing, for example, 64 bits (i.e., one for each of the queues). In this case, OR gate 520 generates a queue vector that contains all zeroes except for the bits representing queues 17-20. From this vector, dequeue logic 330 may determine from which queues to read data. In other words, dequeue logic 330 may read or otherwise process data from one or more of queues 17-20.

Figure 7:
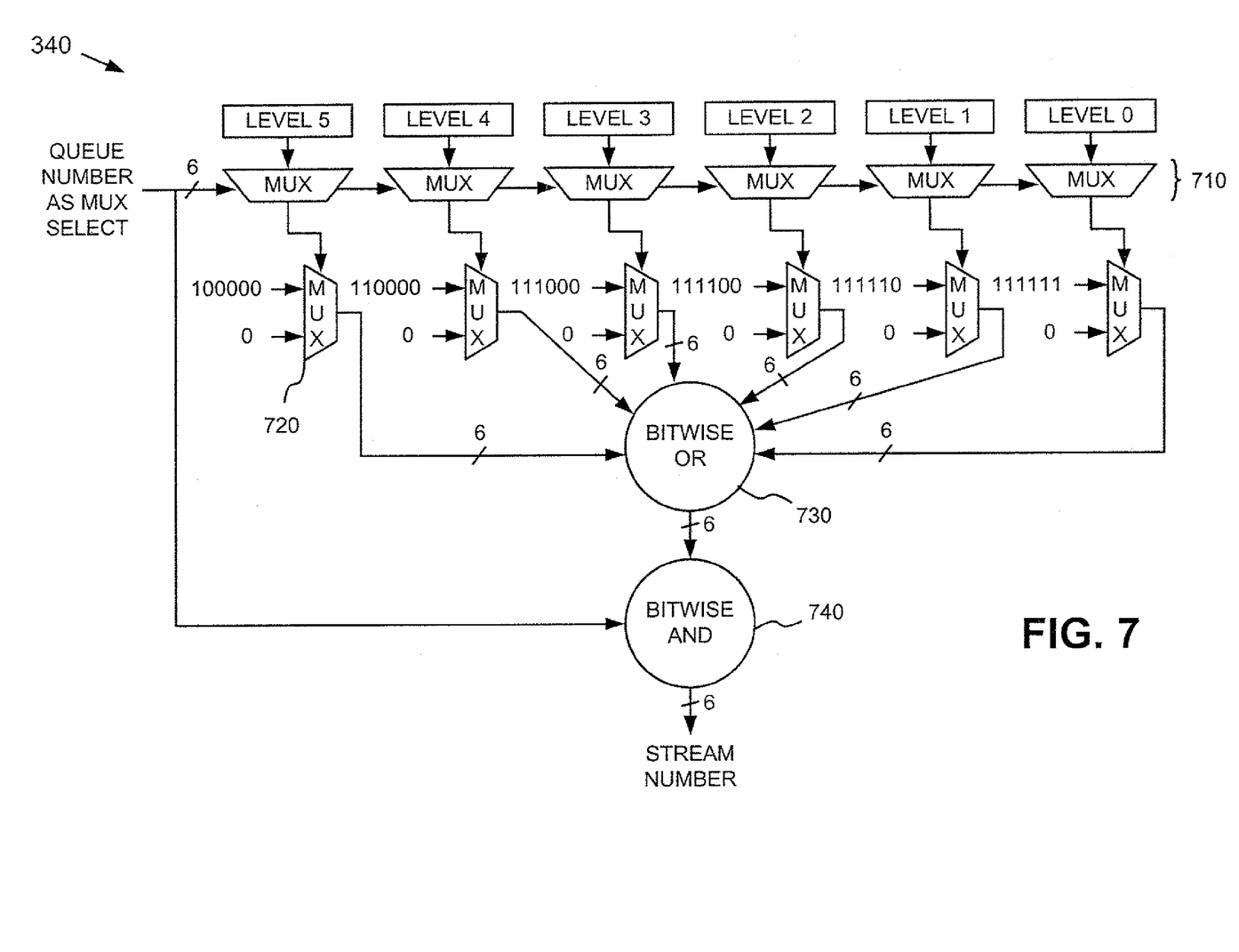
FIG. 7 is an exemplary diagram of queue-to-stream logic of FIG. 3 according to an implementation consistent with the principles of the invention.

FIG. 7 is an exemplary diagram of Q/S logic 340 according to an implementation consistent with the principles of the invention. Q/S logic 340 may include multiplexers 710, multiplexers 720, OR gate 730, and AND gate 740. Each of multiplexers 710 and 720 corresponds to one of the levels 0 through 5 of streams shown in FIG. 4.

A multiplexer 710 receives a 64-bit level vector associated with the corresponding level from a memory. The level vectors may be generated as follows:

level 0={S63_mask, 1b0, S61_mask, 1b0, ..., S3_mask, 1b0, S1_mask, 1b0} level 1={S62_mask, 2b0, S58_mask, 2b0, ..., S6_mask, 2b0, S2_mask, 2b0} level 2={S60_mask, 4b0, S52_mask, 4b0, ..., S12_mask, 4b0, S4_mask, 4b0} level 3={S56_mask, 8b0, S40_mask, 8b0, S24_mask, 8b0, S8_mask, 8b0} level 4{S48_mask, 16b0, S16_mask, 16b0} level 5={S32_mask, 32b0} where S#_mask corresponds to the mask for stream #, and #b0 corresponds to a number of bits of a predetermined value, such as zero. Each of multiplexers 710 receives a queue number as a select address to select one bit of the 64-bit input.

Each of the outputs of multiplexers 710 is supplied as a select address to one of multiplexers 720. Multiplexer 720 selects between a value of zero and a predetermined value, which may be unique for each level, as shown in FIG. 7. For example, the predetermined value for level 5 is 100000, for level 4 is 110000, for level 3 is 111000, etc. If the output of multiplexer 710 is a one (meaning that the queue number is in that level), then multiplexer 720 outputs its predetermined value to OR gate 730. Otherwise, multiplexer 720 outputs a zero to OR gate 730.

OR gate 730 performs a bitwise OR operation on the multiplexer outputs to generate a vector that it provides to AND gate 740. The output vector from OR gate 730 identifies the level to which the queue corresponds. AND gate 740 performs a bitwise AND operation on the output vector from OR gate 730 and the queue number. The result of the AND operation is the stream number to which the queue identified by the queue number is assigned.

Figure 8:
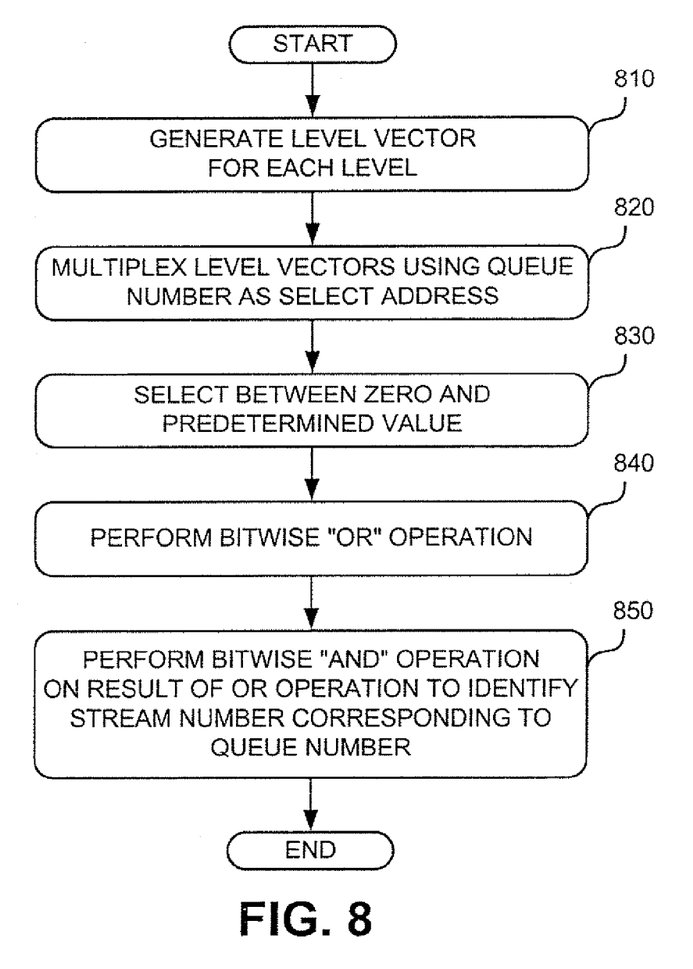
FIG. 8 is a flowchart of exemplary processing for queue-to-stream mapping according to an implementation consistent with the principles of the invention.

FIG. 8 is a flowchart of exemplary processing for queue-to-stream mapping according to an implementation consistent with the principles of the invention. Processing may begin with Q/S logic 340 generating a level, vector for each of the levels in the queue-to-stream assignment illustrated in FIG. 4 (Act 810). The level vectors may be generated based on the stream masks as described above.

Each of multiplexers 710 may receive a level vector and output a value based on a queue number used as a select address (Act 820). The queue number used is the queue number for which the corresponding stream number is desired. Each multiplexer 710 may output a single value to multiplexer 720. Multiplexer 720 may use the output of multiplexer 710 as a select address to select either a zero or a predetermined (unique) value (Act 830). Each multiplexer 710 may output its value to OR gate 730.

OR gate 730 may perform a bitwise OR operation on the outputs of multiplexers 720 (Act 840). As a result of the OR operation, OR gate 730 generates a vector that it supplies to AND gate 740. AND gate 740 may perform a bitwise AND operation on the queue number and the output of OR gate 730 to identify a stream number that corresponds to the queue number (Act 850).

As an example, suppose that we desire to determine to which stream queue 17 is assigned. As shown in FIG. 4, queue 17 may be assigned to stream 0, 16, or 17. As in the previous example, suppose that queues 17-20 are assigned to stream 16, as evidenced by its mask of: 0000000000011110. The level vectors are created from the masks, as described above. Each of multiplexers 710 selects one bit of the corresponding level vector using the queue number 17 as a select address. In this case, the multiplexers corresponding to levels 0-3 and 5 output a zero, and the multiplexer corresponding to level 4 outputs a one.

Multiplexers 720 use the outputs of multiplexers 710 as select addresses. In this case, the multiplexers corresponding to levels 0-3 and 5 output a zero value to OR gate 730. The multiplexer corresponding to level 4, however, outputs a predetermined value, such as 110000, to OR gate 730.

OR gate 730 performs a bitwise OR operation on the output of multiplexers 710 to generate a vector having the following bits: 110000. The vector uniquely corresponds to one of the levels. AND gate 740 performs a bitwise AND operation on the vector from OR gate 730 (i.e., 110000) and the queue number 17 (i.e., 010001) to generate the stream number (i.e., 010000). In this case, AND gate 740 determines that queue number 17 is assigned to stream 16.

The simple hardware configurations described with regard to FIGS. 5 and 7 permit stream numbers to be mapped to queue numbers and queue numbers to be mapped to stream numbers, respectively, in a fast and low cost manner regardless of the number of streams or queues.

CONCLUSION

Systems and methods, consistent with the principles of the invention, provide stream-to-queue and queue-to-stream mapping in a fast and low cost manner. To facilitate the mapping, queues are preliminarily assigned to one or more streams and masks are defined to provide the particular assignments of queues to streams.

The foregoing description of preferred embodiments of the present invention provides illustration and description, but is not intended to be exhaustive or to limit the invention to the precise form disclosed. Modifications and variations are possible in light of the above teachings or may be acquired from practice of the invention. For example, systems and methods have been described in the context of a network device. In other implementations consistent with the principles of the invention, the systems and methods described herein may be applicable to other types of devices or systems.

Further, certain portions of the invention have been described as "logic" that performs one or more functions. This logic may include hardware, such as an application specific integrated circuit, software, or a combination of hardware and software.

No element, act, or instruction used in the description, of the present application should be construed as critical or essential to the invention unless explicitly described as such. Also, as used herein, the article "a" is intended to include one or more items. Where only one item is intended, the term "one" or similar language is used. The scope of the invention is defined by the claims and their equivalents.

What is claimed is:

1. A system for identifying a stream corresponding to a queue identifier for one of a plurality of queues, each of the queues being assigned to one of a plurality of streams, the system comprising:

a plurality of multiplexers, each of the multiplexers to receive a level vector associated with one or more of the streams and the queue identifier and output a data value;

a first logical operator to perform a first logical operation on the data values from the multiplexers to generate an output vector, where the first logical operator includes an OR gate; and a second logical operator to perform a second logical operation on the queue identifier and the output vector from the first logical operator to identify one of the streams that corresponds to the queue identifier.

2. The system of claim 1, where each of the multiplexers is to use the queue identifier to select a portion of the level vector.

3. The system of claim 1, where each of the level vectors is generated from one or more masks associated with the one or more streams, each of the one or more masks identifying one or more of the queues assigned to the associated one of the one or more streams.

4. A system for identifying a stream corresponding to a queue identifier for one of a plurality of queues, each of the queues being assigned to one of a plurality of streams, the system comprising:
- a plurality of multiplexers, each of the multiplexers to receive a level vector associated with one or more of the streams and the queue identifier and output a data value;
- a first logical operator to perform a first logical operation on the data values from the multiplexers to generate an output vector; and
- a second logical operator to perform a second logical operation on the queue identifier and the output vector from the first logical operator to identify one of the streams that corresponds to the queue identifier, where the second logical operator includes an AND gate.

5. A method for identifying a stream corresponding to a queue identifier for one of a plurality of queues, each of the queues being assigned to one of a plurality of streams, the method comprising:
- generating a plurality of level vectors, each of the level vectors being associated with one or more of the streams;
- selecting a portion of each of the level vectors based on the queue identifier;
- performing a first logical operation on the selected portions to generate an output vector, where performing the first logical operation includes performing an OR operation on the selected portions; and
- performing a second logical operation on the queue identifier and the output vector to identify one of the streams that corresponds to the queue identifier.

6. The method of claim 5, where generating the plurality of level vectors includes:
- identifying one or more masks corresponding to the one or more streams associated with each of the level vectors, the one or more masks identifying one or more of the queues assigned to the one or more streams, and
- using the identified one or more masks to generate each of the plurality of level vectors.

7. A method for identifying a stream corresponding to a queue identifier for one of a plurality of queues, each of the queues being assigned to one of a plurality of streams, the method comprising:
- generating a plurality of level vectors, each of the level vectors being associated with one or more of the streams;
- selecting a portion of each of the level vectors based on the queue identifier;
- performing a first logical operation on the selected portions to generate an output vector, where performing the first logical operation includes performing an OR operation on the selected portions;
- performing a second logical operation on the queue identifier and the output vector to identify one of the streams that corresponds to the queue identifier, where performing the second logical operation includes performing an AND operation on the queue identifier and the output vector.

8. A memory that stores data corresponding to a plurality of streams, the memory comprising:
- a plurality of queues to store the data, each of the queues being assigned to one of the streams based on a queue-to-stream assignment;
- stream-to-queue logic to identify which of the queues has data to be processed;
- dequeue logic to process data in the identified queues; and
- queue-to-stream logic to identify which of the streams correspond to the identified queues, where the queue-to-stream logic includes:
  - a plurality of first multiplexers, each of the first multiplexers to receive a level vector associated with one or more of the streams and a queue identifier corresponding to one of the identified queues and output a select signal,
  - a plurality of second multiplexers, each of the second multiplexers to output a data value based on one of the select signals,
  - a first logical operator to perform a first logical operation on the data values from the second multiplexers to generate an output vector, and
  - a second logical operator to perform a second logical operation on the queue identifier and the output vector from the first logical operator to identify one of the streams that corresponds to the queue identifier.

9. The memory of claim 8, where each of the level vectors is generated from a mask associated with the one or more streams, the mask identifying one or more of the queues assigned to the one or more streams.

10. The memory of claim 8, where the first logical operator includes an OR gate.

11. The memory of claim 8, where the second logical operator includes an AND gate.

* * * * *